United States Patent [19]
Peclier et al.

[11] Patent Number: 5,606,410
[45] Date of Patent: Feb. 25, 1997

[54] METHOD FOR CONTROLLING THE SURFACE STATE OF ONE FACE OF A SOLID AND THE ASSOCIATED DEVICE

[75] Inventors: Roger Peclier, Faverges de lu Tour; Pierre Laurent, St. Georges de Commiers; Jean-François Piquard, Montchaboud, all of France

[73] Assignee: Compagnie Generale des Matieres Nucleaires, Velizy-Villacoublay, France

[21] Appl. No.: 436,349
[22] PCT Filed: Nov. 4, 1994
[86] PCT No.: PCT/FR94/01277
  § 371 Date: Jul. 26, 1995
  § 102(e) Date: Jul. 26, 1995
[87] PCT Pub. No.: WO95/12810
  PCT Pub. Date: May 11, 1995

[30] Foreign Application Priority Data

Nov. 4, 1993 [FR] France .................. 93 13128

[51] Int. Cl.⁶ .................................................. G01N 21/00
[52] U.S. Cl. .......................... 356/237; 356/388; 356/392; 356/394
[58] Field of Search .................. 356/237, 388, 356/392, 394, 256

[56] References Cited

U.S. PATENT DOCUMENTS

| | | | |
|---|---|---|---|
| 3,864,564 | 2/1975 | Adkins | 250/201 |
| 4,451,929 | 5/1984 | Yoshida | 382/15 |
| 4,733,963 | 3/1988 | Date et al. | 356/237 |

FOREIGN PATENT DOCUMENTS

| | | |
|---|---|---|
| 8500657 | 2/1985 | WIPO. |
| 9104634 | 4/1991 | WIPO. |

OTHER PUBLICATIONS

"Mikromechanische Strukturen Optisch Messen", Feinwerktechnik & Messtechnik, vol. 100, No. 6, Jun. 1992, pp. 255–258.

Primary Examiner—Frank Gonzalez
Assistant Examiner—Reginald A. Ratliff
Attorney, Agent, or Firm—Pearne, Gordon, McCoy & Granger

[57] ABSTRACT

A method and apparatus for checking the surface state of one face (2) of a solid (1) in order to locate shape defects which may be present therein. The observation of the face to be checked takes place by means of photography using a large field video camera (3) and a small field video camera (4). The size of the located defects is measured by an optoelectronic sensor or probe (11). The apparatus can be controlled by an operator or can have automatic control.

14 Claims, 2 Drawing Sheets

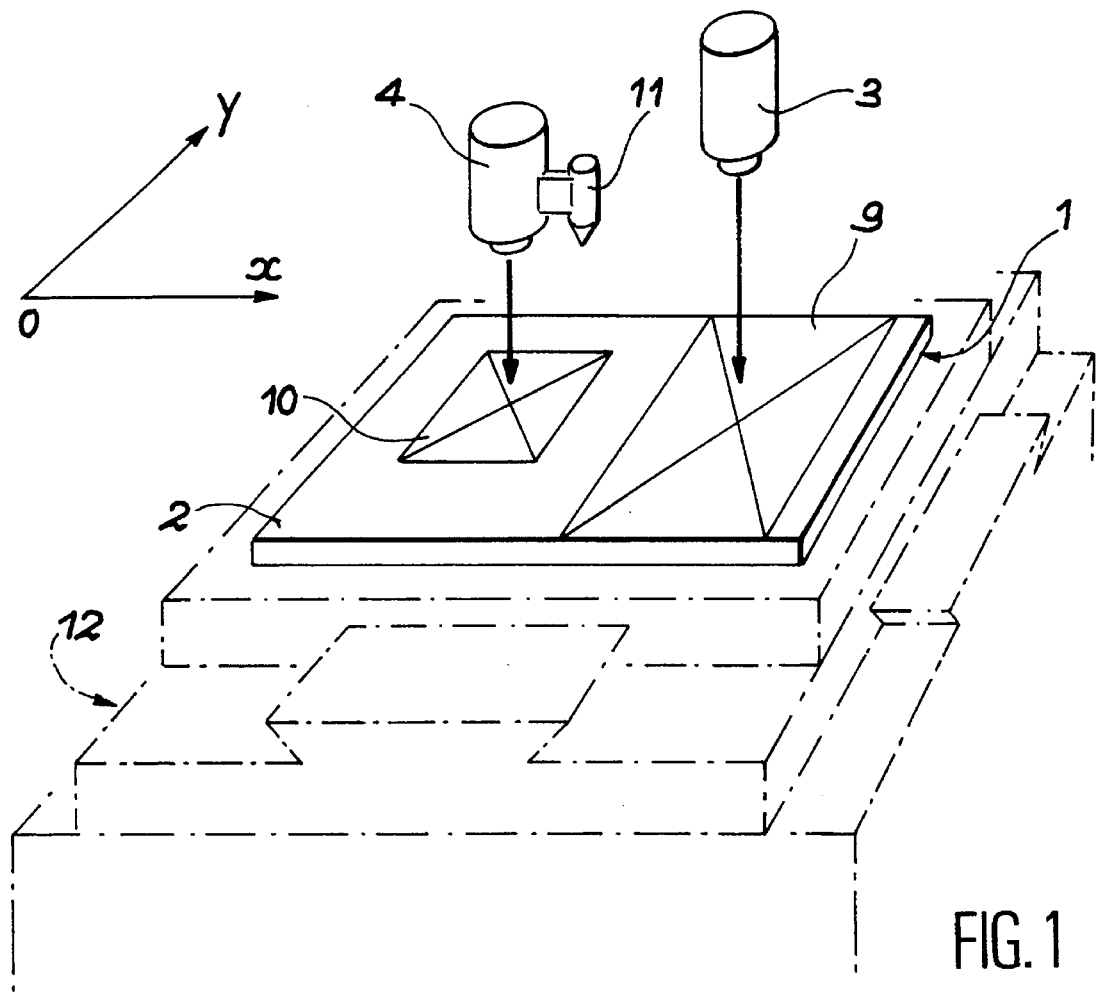
FIG. 1
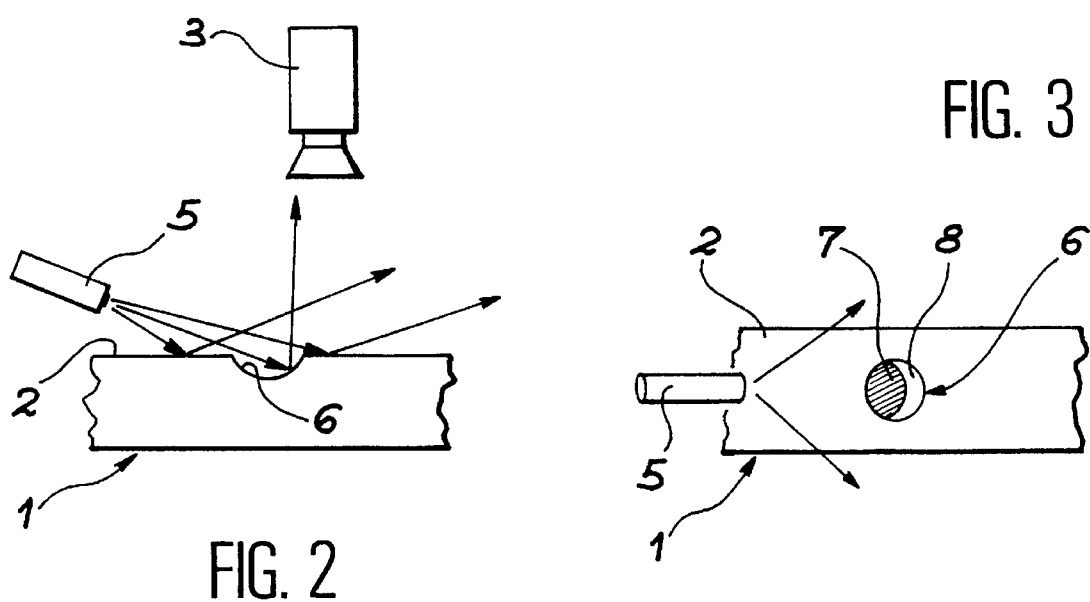
FIG. 3
FIG. 2

METHOD FOR CONTROLLING THE SURFACE STATE OF ONE FACE OF A SOLID AND THE ASSOCIATED DEVICE

The present invention relates to a method for controlling or checking the surface state of one face of a solid. It also relates to a device for performing this method and intended both for equipment assisting an operator and for an automatic control installation.

BACKGROUND OF THE INVENTION

For various reasons, it is often necessary to control, inspect or check the surface state of one or more faces of a solid and this is more particularly the case with laminated nuclear fuel.

One variety of nuclear fuel for experimental reactors is constituted by aluminium sandwich plates with a core made from a mixture of uranium and aluminium. The production process of said plates consists of laminating together four components, namely a compacted aluminium and uranium core mounted in a frame and covered by two plates forming a cover.

Although highly industrial, this production process requires several manual operations and know-how, so that there are variations in the quality of manufacture. However, as these products are particularly sensitive, they require very precise characteristics imposed by the users. These requirements concerning quality give rise to internal and external controls of the fuel plates.

The internal control takes place by special machines using ultrasonics or X-rays. The control takes place automatically and gives rise to reports combining quantitative and calibrated measurements.

The external control has hitherto been performed visually by qualified operators. The procedure involves observing two surfaces of a plate under glancing light, whilst manipulating the plate and locating or pinpointing surface defects. The latter are holes or scratches, whose depth must not exceed 100 µm. When a surface defect appears suspect to the operator, he places the plate beneath the objective of a microscope and evaluates the maximum depth of the hole or scratch previously located. Plates having characteristics falling outside the standard are disposed of as waste. Certain users have particularly strict requirements, which requires a supplementary control performed by another team.

This external control, which is entirely the responsibility of human evaluation, suffers from a number of disadvantages. It is fastidious and tiring due to the concentration and acuity required. Its reliability is dependent on the state of vigilance, which varies in time and between individual operators. In the case of a second control, when the quality tends towards 100%, it remains virtually impossible to maintain the necessary vigilance for detecting the very rare defect or objectively impose acceptance limits. In addition, visual measurements offer no quantitative and objective basis for the support of a control or inspection report.

The invention makes it possible to improve the control of surface states and is applicable both to equipment used by an operator and to an automatic control installation. The observation conditions are improved by photographing the surfaces to be controlled, said photographs either being presented on a video screen at a control station, or are digitally processed in the case of an automatic control installation. The use of an optoelectronic probe makes it possible to obtain objective and quantitative depth measurements, which can be recorded.

SUMMARY OF THE INVENTION

The invention therefore relates to a method for controlling the surface state of one face of a solid for locating shape defects liable to be located there and comprising:
  observing the face of the solid in order to locate areas liable to constitute defects,
  observing said areas using optical magnification means,
  evaluating the size of these areas to determine, by comparison with a given limit size implying the existence of a defect, if said areas are or are not defects,
characterized in that:
  the observations take place by photography,
  the evaluation of the size of the areas liable to constitute defects takes place by measurement using an optoelectronic probe.

The observation of the face of the solid advantageously takes place under glancing, multidirectional illumination.

Preferably, photography or filming takes place by video and in two successive stages, a first or so-called large field analysis stage makes it possible to rapidly pinpoint all the areas liable to constitute defects and a second or so-called small field analysis stage, which only applies to the areas pinpointed in the first stage, the small field analysis constituting the observation by the magnification means.

The measurement performed by means of the optoelectronic probe can be recorded.

The invention also relates to a device for performing this control method comprising:
  means for the reception of the solid permitting a presentation of the face of the solid to be observed,
  means for illuminating said face,
  a large field video camera for observing said face,
  a small field video camera for observing said face,
  means for processing the output signals supplied by the video cameras, said processing means supplying informations on the shape defects liable to occur on said face,
  an optoelectronic probe controlled by control means receiving said informations.

This device can also incorporate means for eliminating the dust liable to be present on said face.

The reception means can comprise a plate for the translation of the solid permitting the displacement of said face in accordance with two crossed axes.

The translation plate can be used for the displacement of the said face in accordance with one of the two axes for the large field video camera and according to both axes for the small field video camera and for the optoelectronic probe.

With a view to a control by an operator, the means for processing the output signals supplied by the video cameras can comprise two monitors, one for displaying the view filmed by the large field video camera and the other for displaying the view filmed by the small field video camera.

In this case, the device can incorporate means for displaying values measured by the optoelectronic probe.

The reception means incorporating a plate for translating the solid permitting the displacement of said face in accordance with two crossed axes, the device can incorporate means for controlling said plate in accordance with these axes operating in the manual mode or in the automatic mode.

It can incorporate means for recording positions of areas liable to constitute shape defects and measurements of the probe.

With a view to an automatic control, the device can be equipped with a data processing control system, which processes the output signals supplied by the video cameras, locates on the basis of these signals the areas liable to constitute shape defects, controls the optoelectronic probe and analyses the measurements given by the probe.

BRIEF DESCRIPTION OF THE DRAWINGS

The invention is described in greater detail hereinafter relative to non-limitative embodiments and with reference to the attached drawings, wherein show:

FIG. 1 the method for controlling one face of a plate for pinpointing any shape defects according to the invention.

FIGS. 2 and 3 respectively profile and plan views of a plate to be controlled illuminated with glancing light in one direction.

DETAILED DESCRIPTION OF THE PREFERRED EMBODIMENTS

Figure 4:
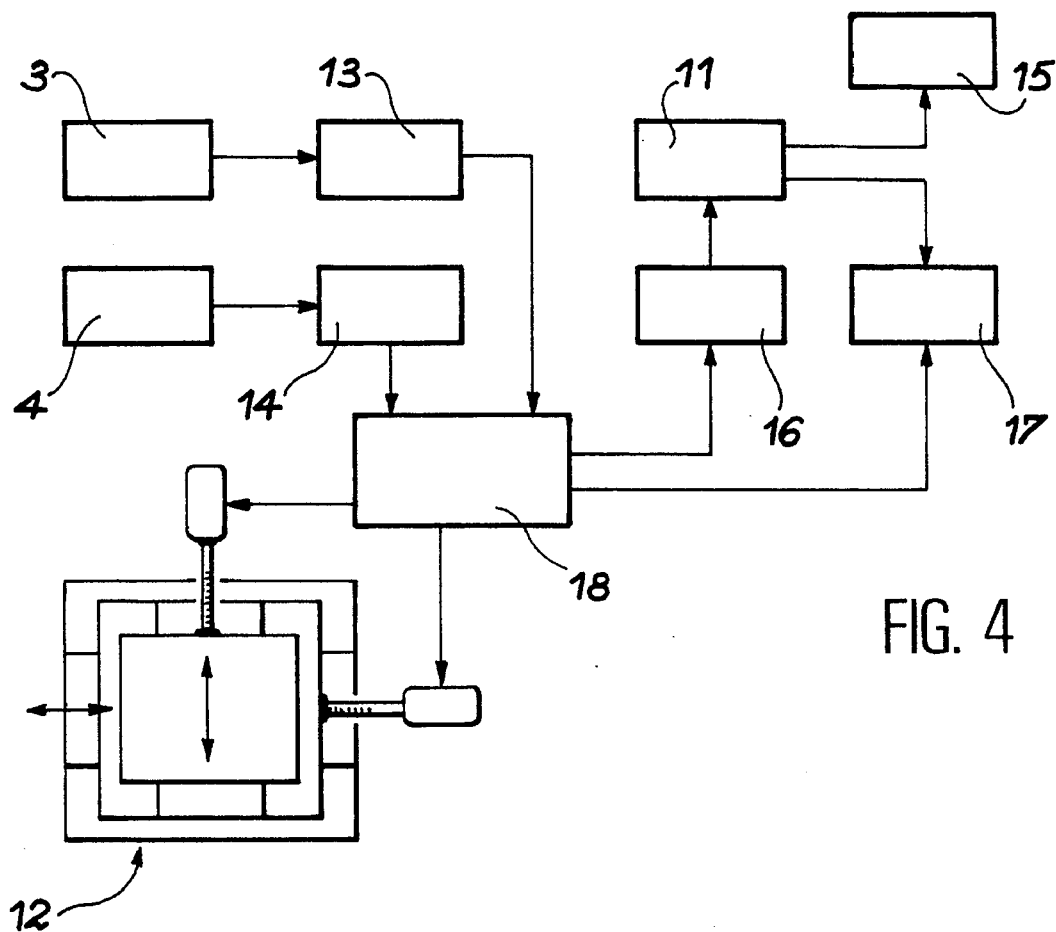
FIG. 4 a block diagram of a device for performing the control method according to the invention and usable for assisting an operator.

FIG. 1 shows a plate and it is wished to control or check the surface state of its face 2 by firstly observing the said face.

According to the invention this observation takes place by means of photography or filming. One satisfactory solution consists of using two video cameras, one for performing a large field analysis and the other for performing a small field analysis.

The large field camera 3 makes it possible to pinpoint and locate each potential defect rapidly and with an accuracy of e.g. approximately 200 μm. The small field camera 4 only processes the zones of the large field image having suspected areas. It permits a very accurate analysis and location, e.g. with a precision of approximately 20 μm.

The face to be observed is illuminated by a glancing, multidirectional illumination equipment constituted by several light sources creating a homogeneous illumination. The latter acts on the discontinuities of the surface state by overillumination or shadow, forming local contrasts which would constitute location references. FIGS. 2 and 3 illustrate this type of illumination for a single lamp 5. In this case, the camera 3 intersects an image of the defect 6 exposed to said illumination and comprising a dark area 7 and a light area 8. In practice, use will be made of four light sources arranged in perpendicular directions.

In this embodiment, the large field video camera 3 covers the width of the plate 1, i.e. a surface such as that carrying the reference numeral 9 in FIG. 1 and which can be 100 mm×70 mm. The small field video camera 4 covers a smaller surface 10 than the surface 9 and which can be 12 mm×9 mm.

The device incorporates an optical probe or sensor 11 of the focodyne type (i.e. control of the focal spot of a laser diode), whose measurement beam diameter is much smaller than the size of the areas considered as defects.

The type of illumination used gives excellent results on cavity defects, but is very sensitive to dust which can be deposited on the plate. Thus, use is made of a dust elimination unit, e.g. by brushing and suction.

The plate is placed on a translation plate member 12 having two perpendicular, motorized axes X and Y making it possible to accurately know the position of the plate with respect to a reference point. It is possible for this purpose to use the rotation angle of the drive motors for the axes or shafts or an incremental coder. The displacement of the plate member 12 is regulated by an axis or shaft control member.

The plate can be maintained on the plate member 12 by vacuum. It can be displaced according to the axis X under the large field camera 3 and according to the axes X and Y under the small field camera 4, as well as under the probe 11.

For an operator-based control station corresponding to the diagram of FIG. 4, the device can be completed by two different video monitors, one monitor 13 for the image transmitted by the large field camera 3 and one monitor 14 for the image transmitted by the small field camera 4. A display device 15 permits the reading of the values measured by the probe 11.

The control then takes place in the following way. The operator observes on the "large field" video monitor the illuminated plate and made to move rapidly by the shaft control member 18 in front of the fixed, large field camera 3. When it detects a suspect area, it stops the movement and points out the located point on the screen 13 and then continues the rapid run up to the end of the plate.

On return, the plate automatically positions in the small field camera 4 the previously pinpointed locations. The operator observing the "small field" video monitor 14 does or does not confirm the defects and starts the measuring procedure by means of the control member 16 of the optical probe 11. The values of the measurements and the location Of the defects are recorded by the recorder 17 for drafting a control report.

Figure 5:
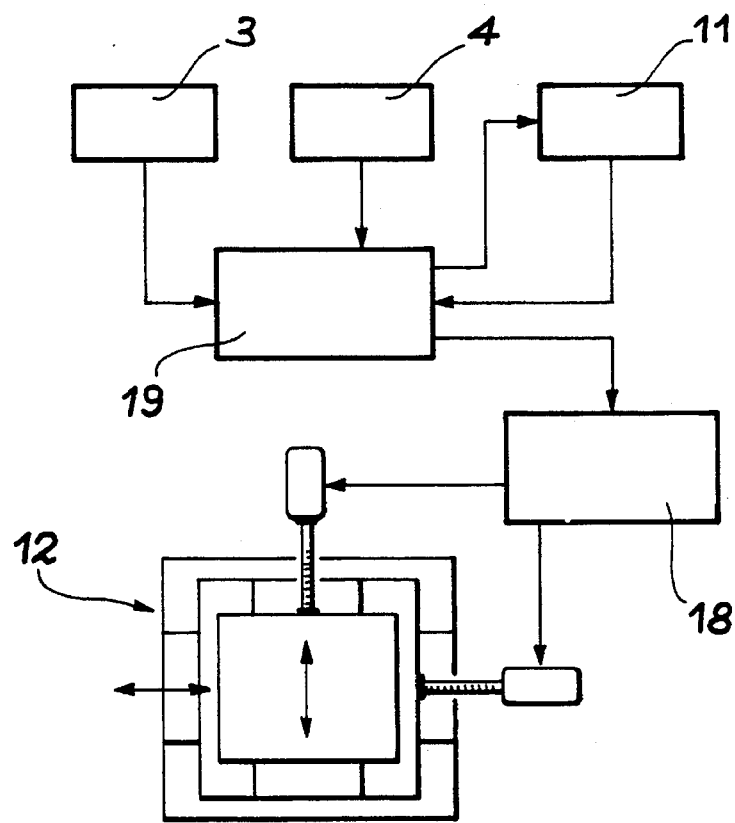
FIG. 5 a block diagram of a device for performing the control method according to the invention and usable for automatic control purposes.

In an automatic control installation corresponding to the diagram of FIG. 5, the aforementioned equipment is supplemented by a data processing system 19. This system controls the installation, processes the video signals transmitted by the cameras 3 and 4, performs the automatic diagnosis and analyses the measurements of the probe 11. A control report is also drafted.

For automatic detection, the performance method can be summarized as follows. A first rapid run takes place in accordance with a succession of exposures, whose field corresponds to that of the large field camera. The defects and remaining dust appear white on a grey background. A first processing by mathematical morphology consists of extracting the background from the image. The latter is then removed from the original image, which now only reveals the defects. A second run positions the defects beneath the small field camera. Each image is processed in order to accurately pinpoint these defects and position the probe. The probe then performs a profile plotting of the defect and a maximum calculation is performed on the series of measurements.

In exemplified manner an automatic control installation was produced on the basis of the following components. An INTEL 80386 computer was used at 25 MHz and to it was added a card permitting the acquisition and processing of 512×512 point images coded on 8 bits (i.e. 256 grey levels). The motorized stage permitting the large field displacement is constituted by two perpendicular tables having a travel of 120 mm, a resolution of 1 μm and a displacement speed of 2 mm/s. The illumination of the plate takes place by two cold light generators coupled to two optical fibres, which gives four homogeneous light sources.

As the test plate dimensions were 70×780 mm, it was necessary to process eight large fields per face. Prior to each large field analysis, the plate was cleaned with alcohol and then blown with compressed air in order to eliminate the maximum of traces and dust.

The aim of the large field analysis is to pinpoint defects which may exist on the plate. The camera acquires a 100×70 mm field. On said image, the defects appear in white on a grey background. The binarization of the image (white defects on a black background) takes place by mathematical morphology methods. The image is firstly eroded (N times) and then expanded (N times). This gives image no. 2 from which the defects have been eliminated. This image is removed from the initial image and then the result is thresholded. The number N of erosions and expansions, as well as the height of the threshold are parameters which can easily be modified by the user.

The binarized image is filtered so as to eliminate spots with a surface below a given threshold. If the thus obtained binary image reveals no defect (white spots), the following field is brought under the camera and the large field analysis phase is restarted. In the opposite case, the centre of each spot is calculated and then positioned beneath the objective or lens of the small field camera.

The small field analysis is used for very accurately determining the displacement of the optical microprobe. The small field camera is equipped with a lens examining a field with a surface of 12×9 mm (i.e. a resolution of approximately 20 μm). Small field acquisition is performed in the same way as large field acquisition.

The processing of the small fields is in two different forms as a function of the image type.

If the image has a large defect (wide scratch or large diameter hole), its histogram has two distinct peaks, the first in the low grey levels corresponding to defects and the second in the white corresponding to the background of the image. Thus, it is possible to calculate on the basis of said histogram a threshold permitting the binarization of the image in a global manner. In the opposite case, a local processing is performed.

If the histogram has not permitted the calculation of a binarization threshold (defects too small, lack of contrast, inhomogeneity of illumination), an area-based processing algorithm is used. This algorithm functions by area comparison. Twenty five integrated, horizontal profiles of twelve lines and which partly overlap are calculated on the image. These profiles make it possible to define a maximum and minimum profile of the image.

A thresholding on the difference of the maximim and minimum profiles permits the calculation of the position of the defect on the X axis. A vertical, integrated profile of the window [(Xd,0); (Xf,512)] is then calculated on the Y axis. The window [(Xd,Yd); (Xf,Yf)] surrounding the defect is thus accurately determined.

All the parts outside the window of the image are placed at zero and then the windows are binarized. This gives a binary image as in the case of global processing.

A defect is likened to a hole if its length/width ratio is between 1−a and 1+a, the value of a being a parameter of the system defined by the user. In this case, two perpendicular depth measurements passing through the centre of the hole are calculated as a result of the displacement via a motorized stage of an optical microprobe.

The defects which cannot be likened to holes are taken into account as scratches. The investigation of the depth of a scratch takes place by calculating the maximum depth of a series of measurements. If the length of the scratch is below 5 mm, a profile is calculated every millimetre, otherwise every 2.5 mm.

Once the binarization of the small field image has taken place, an analysis of the surface and roundness of the defects makes it possible to classify them and select an optimum search mode for their depth.

We claim:

1. Method for checking the surface state of one face (2) of a solid (1) for locating shape defects which may be present therein, said method comprising the steps of:

observing the face of the solid using photography in order to locate an area that may be a defect;

observing said area using photography and optical magnification means; and measuring the size of the area with an optoelectronic probe; and comparing the size of the area with a predetermined size limit to determine whether the area is a defect, said area being considered a defect if the size of the area is larger than the predetermined size limit.

2. Method according to claim 1, wherein the observation of the face of the solid takes place under a glancing, multidirectional illumination.

3. Method according to claim 1 wherein the steps of observing the face and the area by photography takes place in video and are done successively, and wherein the step of observing the face comprises a first or large field analysis stage making it possible to rapidly locate all areas that may be defects, and wherein the step of observing the area comprises a second or small field analysis stage only applying to the areas detected in the first stage.

4. Method according to claim 1 further comprising the step of recording the measurement made by means of the optoelectronic probe (11).

5. Device for checking the surface state of one face (2) of a solid (1) for locating shape defects, said device comprising:

means for receiving the solid (1) to permit a presentation of the face of the solid to be observed;

means for illuminating said face;

a large field video camera (3) for the observation of said face;

a small field video camera (4) for the observation of said face;

means for processing output signals supplied by the video cameras, said processing means supplying information on shape defects that might be present on said face;

an optoelectronic probe (11); and means for controlling the optoelectronic probe, said controlling means receiving the information from said processing means.

6. Device according to claim 5 further comprising means for eliminating dust which may be present on said face.

7. Device according to claim 5 wherein the receiving means comprise a translation plate member (12) for translating the solid, thereby permitting the displacement of said face in accordance with two crossed axes.

8. Device according to claim 7 wherein the translation plate member (12) ensures the displacement of said face in accordance with one of the two axes for the large field video camera and in accordance with both axes for the small field video camera and for the optoelectronic probe.

9. Device according to claim 5 wherein the means for processing the output signals supplied by the large field and small field video cameras (3, 4) comprise first and second monitors, said first monitor displaying a view filmed by the large field video camera and said second monitor displaying a view filmed by the small field video camera.

10. Device according to claim 9 further comprising means (15) for displaying values measured by the optoelectronic probe.

11. Device according to claim 9 wherein the receiving means comprises a plate member for the translation of the solid, thereby permitting the displacement of said face in accordance with two crossed axes, and wherein the device further comprises means (18) for controlling said plate member in accordance with the axes when the device is operating either in a manual mode or in an automatic mode.

12. Device according to claim 9 further comprising means (17) for recording positions of areas that may be shape defects and for recording measurements of the optoelectronic probe.

13. Device according to claim 5 further comprising a data processing control system (19) that processes the output signals supplied by the large field and small field video cameras (3, 4), locates on the basis of said output signals areas that may be shape defects, controls the optoelectronic probe (11) and analyses measurements given by the optoelectronic probe.

14. Method for checking the surface state of one face (2) of a solid (1) for locating shape defects which may be present therein, said method comprising the steps of:

observing the face of the solid using a large field video camera in order to rapidly locate all areas that may be defects;

observing the areas using a small field video camera and optical magnification means, said step of observing the areas occurring subsequent to the step of observing the face and being limited only to the areas located in the step of observing the face; and measuring the size of the areas with an optoelectronic probe; and comparing the size of the areas with a predetermined size limit in order to determine whether the areas are defects, any one of said areas being considered a defect if it is larger than the predetermined size limit.

* * * * *